United States Patent [19]

Jones et al.

[11] Patent Number: 5,071,438
[45] Date of Patent: Dec. 10, 1991

[54] TIBIAL PROTHESIS WITH PIVOTING ARTICULATING SURFACE

[75] Inventors: Richard E. Jones, Dallas; Joseph S. Skraba; John D. Vinciguerra, both of Austin, all of Tex.

[73] Assignee: Intermedics Orthopedics, Inc., Austin, Tex.

[21] Appl. No.: 610,427

[22] Filed: Nov. 7, 1990

[51] Int. Cl.⁵ ............................................. A61F 2/38
[52] U.S. Cl. ................................... 623/20; 623/18
[58] Field of Search ................. 623/20, 16, 18, 23

[56] References Cited

U.S. PATENT DOCUMENTS

| | | |
|---|---|---|
| 4,136,405 | 1/1979 | Pastrich et al. ................... 623/20 |
| 4,216,549 | 8/1980 | Hillberry et al. .................. 623/20 |
| 4,219,893 | 9/1980 | Noiles ............................ 3/1.911 |
| 4,301,553 | 11/1981 | Noiles ............................ 623/20 |

OTHER PUBLICATIONS

Advertisement, "Link Rotating Total Knee System", *Journal of Bone and Joint Surgery*, Mar. 1985.

*Primary Examiner*—David J. Isabella
*Assistant Examiner*—G. Gualtieri
*Attorney, Agent, or Firm*—John R. Merkling

[57] ABSTRACT

A prosthetic knee with a tibial prothesis comprising a baseplate and an articulating surface which pivots on the baseplate about an axis within a medial condylar compartment.

22 Claims, 2 Drawing Sheets

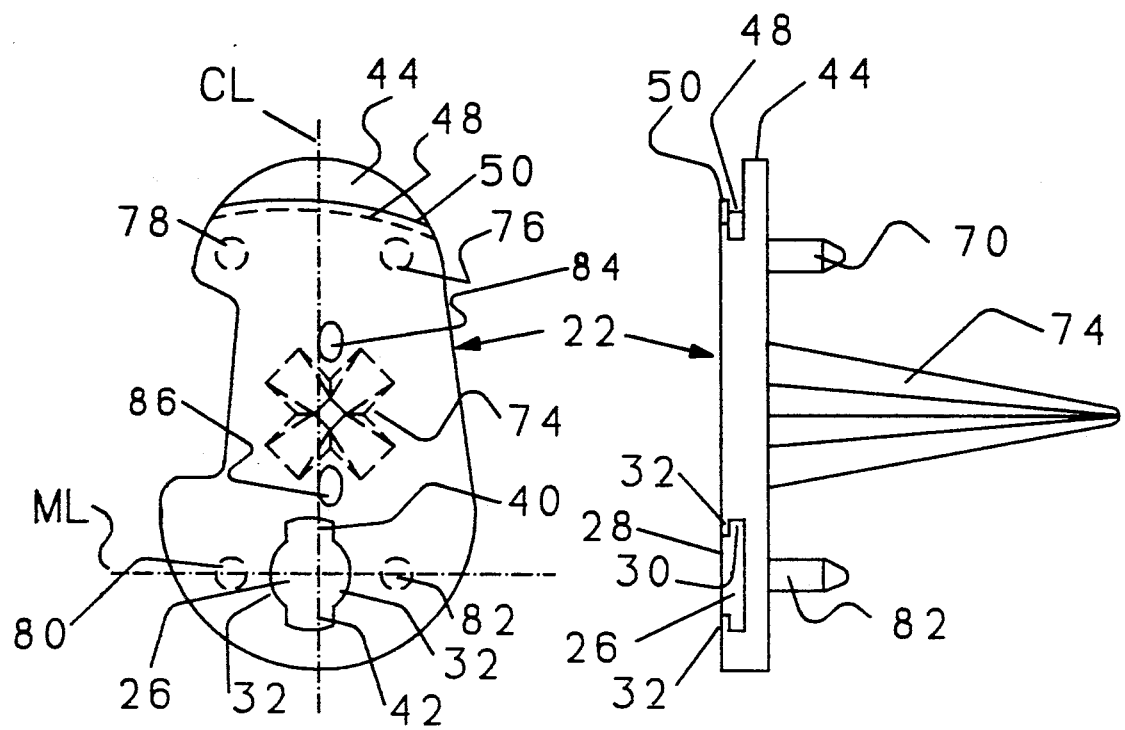
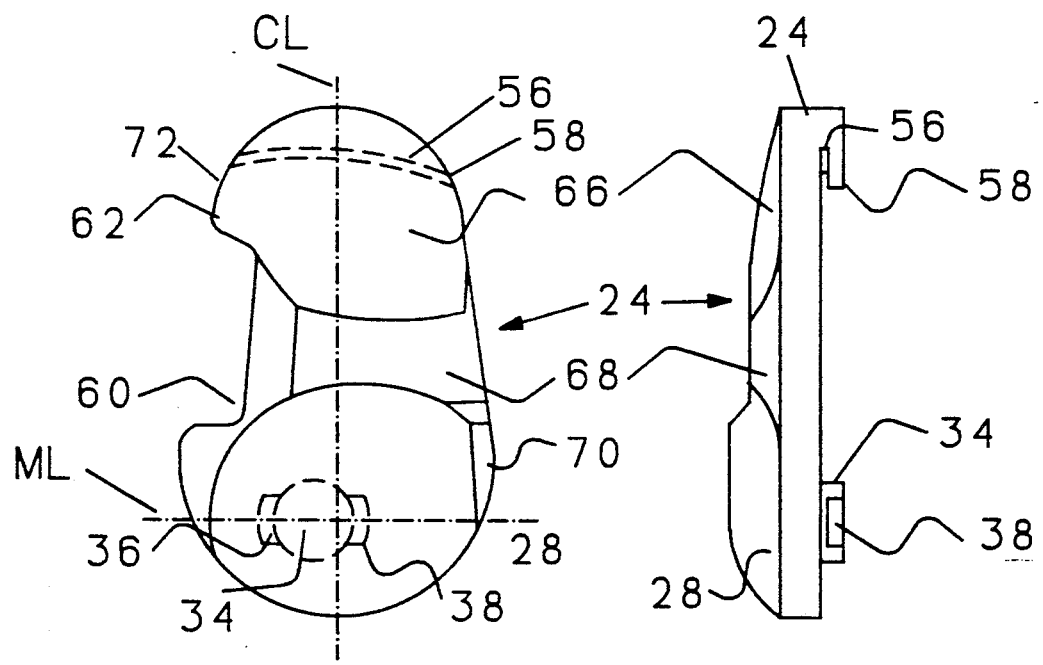

TIBIAL PROTHESIS WITH PIVOTING ARTICULATING SURFACE

BACKGROUND OF THE INVENTION

Our invention is in the general area of orthopedic prostheses, particularly, artificial knees. Specifically, our invention is a tibial prosthesis for an artificial knee. The tibial prosthesis comprises a base plate affixed to an upper, resected surface of a tibia and an articulating surface which pivots about an axis within the medial condylar compartment.

The two largest and longest bones of the human body, the femur and tibia, meet at a person's knee. The tibia is situated at the front and inner side of the lower leg. It is prismoid in form, and expanded above where it enters into the knee joint. The head of the tibia is large and expanded on each side into two eminences, the tuberosities. These eminences form two smooth concave compartments or surfaces which articulate with the condyles of the femur. The medial condyle is more prominent anteriorly and broader both in the anterior-posterior and transverse diameters than the lateral condyle. Accordingly, the lateral articular surface of the tibia is longer, deeper and narrower than the medial surface of the tibia. The medial surface is broader, more circular, and concave from side to side. The anterior surfaces of the tuberosities are continuous with one another, forming a single large surface which is somewhat flattened. Posteriorly the tuberosities are separated from each other by a shallow depression for attachement of ligaments. The medial tuberosity presents posteriorly a deep transverse groove for the insertion of a tendon.

Because of aging or disease, the articulating surfaces of the knee may degrade. To treat certain pathologies, it has become common to surgically remove either the condyles or the tuberosities or both and replace these structures with prosthetic implants.

Tibial prostheses commonly comprise titanium base plates with polyethylene articulating surfaces mounted thereon. To accommodate the range of motion of the human knee, either the femoral condyles or a femoral prosthesis rocks against the articulating surface of the tibial prosthesis. This rocking action can wear away the articulating surface.

Bone cell death (osteolysis) has been linked to polyethylene wear debris. Long-term loosening of implant systems may be caused by osteolysis due to polyethylene debris. Although it is not known if a physiological threshold for wear debris exists, a decrease in the amount wear particles is a positive achievement.

SUMMARY OF OUR INVENTION

We have invented a tibial prosthesis which reduces surface fatigue and wear. Formation of polyethylene debris is reduced and improved longevity of the implant is expected.

The tibial prosthesis consists of a polyethylene insert with an articulating surface and a titanium baseplate. The insert features articulating surfaces which conform closely with the distal femoral condylar surfaces of a femoral prosthesis. We want to have maximum contact area between the femoral prosthesis and the tibial insert between 0° and 20° of flexion. This flexion range occurs during the single leg stance phase in the gait cycle. By achieving maximum contact area during the maximum cyclical load period, we have been able to reduce stress magnitude and thus to reduce wear. Although higher joint forces occur during high flexion activity, such as stair climbing or rising from a chair, the number of cycles of this activity is relatively insignificant when compared to walking cycles.

In the past, increased contact area has been achieved by hinged knee designs which constrain rotary motion. Although normal knees rotate only approximately 10° during gait, past attempts at utilizing hinged knee designs have unduly restricted flexibility. To compensate for highly conforming articulating surfaces, our tibial prosthesis is pivoted so that rotary motion can occur at the insert-baseplate interface. This rotation allow for significant reduction of shear stresses which quickly affect the implant-bone interface in highly conforming or hinged knee designs. The inferior insert surface features a post located under the medial weight bearing area and slightly posterior of the anterior-posterior centerline. The tibial baseplate has a mating feature for the post. The design of the insert-baseplate interface includes locking mechanisms which resist axial disassembly forces.

With the foregoing in mind, it is an object of our invention to provide a knee prosthesis which reduces wear between adjacent articulating surfaces.

Another important object of our invention is to provide a tibial articulating surface of the prosthesis which conforms closely to an adjacent femoral surface.

Another object of our invention is to increase contact area between the tibial prosthesis and a femoral prosthesis to reduce stress levels.

It is a further object of our invention to provide a tibial prosthesis with an articulating surface pivotally mounted on a tibial baseplate.

It is also our object to provide a prosthetic knee wherein the degrees of freedom between the femoral and tibial parts is effectively reduced by incorporating one degree of freedom into the tibial part.

These and other objects and features of our present invention will be apparent from the following detailed description taken with reference to the accompanying drawings.

BRIEF DESCRIPTION OF THE DRAWINGS

FIG. 4 is a top view of a tibial baseplate of the tibial prosthesis of FIG. 2.

FIG. 5 is a through section of the baseplate taken along line 5—5 of FIG. 2.

FIG. 6 is a top view of an insert of the tibial prosthesis of FIG. 2.

FIG. 7 is a rear view of the insert of FIG. 6.

DETAILED DESCRIPTION OF OUR PREFERRED EMBODIMENT

Figure 1:
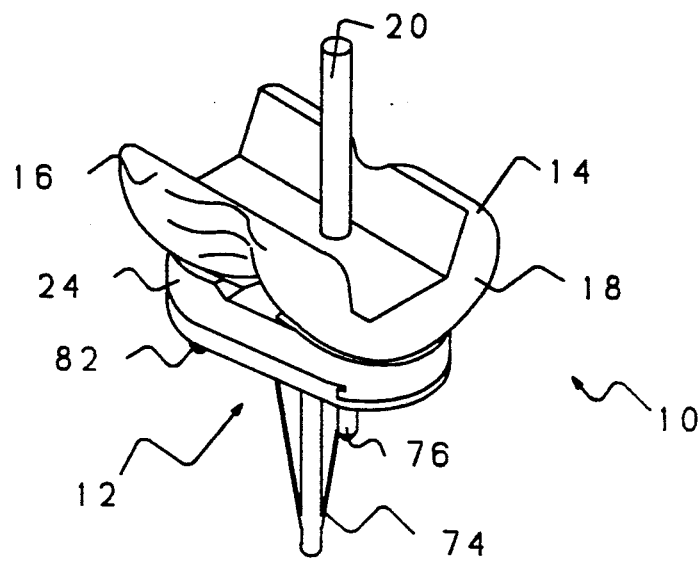
FIG. 1 is a perspective view of a prosthetic knee according to our present invention.

We will now describe our preferred embodiment of our invention by reference to the accompanying drawings. In the drawings, like numerals will refer to like parts in each drawing. FIG. 1 shows a perspective view of a prosthetic knee 10 according to our present invention. A tibial component 12 supports a femoral component 14. The femoral component 14 is not distinctive over the prior art and comprises a medial condylar surface 16 and a lateral condylar surface 18 which replace the natural condyles of a patient's femur. As is known in the art, means should be provided for securing the femoral prosthesis 14 to a resected end of the femur. Such means may comprise a post 20 or cruciate stem.

Figure 2:
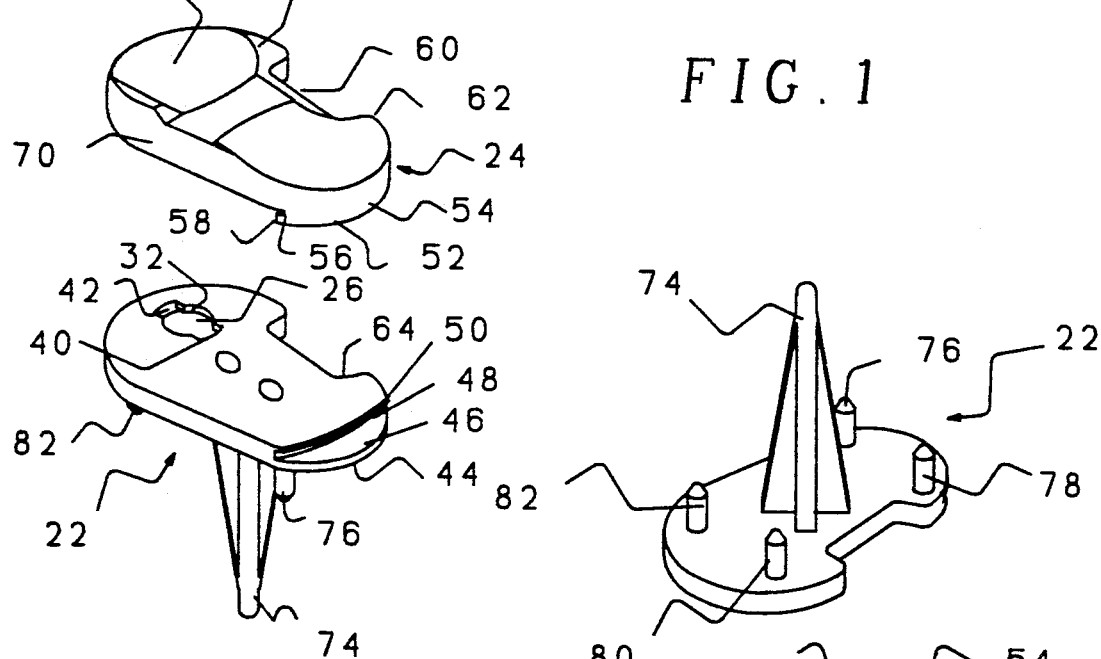
FIG. 2 is an exploded perspective view of a tibial prosthesis.
Figure 3:
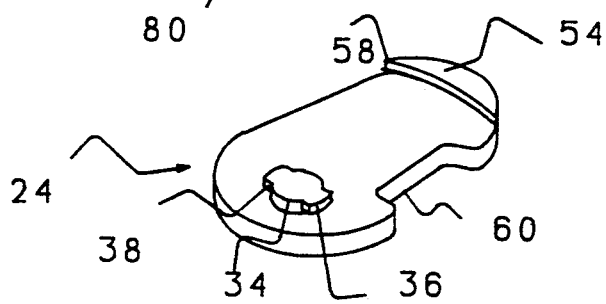
FIG. 3 is antiverted exploded view of the tibial prosthesis of FIG. 2.

The tibial prosthesis 12 comprises a metal baseplate 22 and an ultra high molecular weight polyethylene articulating surface 24. The interaction between these components can be understood with reference to FIGS. 2 and 3. The baseplate 22 has a pivot recess 26 beneath a medial condylar compartment 28 on the articulating surface 24. As can be seen in FIGS. 4 and 6, the overall shape of the medial condylar compartment 28 is generally semicircular. We prefer to locate the pivot recess 26 slightly posterior to a center line CL which bisects the generally semicircular shape of the medial condylar compartment. We also prefer to locate the pivot recess 26 generally on a midline ML perpendicular to the center line CL at a point approximately half of a radius defining the overall semicircular shape of the medial condylar compartment 28. As will be more fully explained below, the articulating surface 24 pivots about the pivoting recess 26. This permits the artificial knee 10 of our invention to compensate for pivotal motion as a patient walks, while maintaining maximum contact between femoral prosthesis 14 and the articulating surface 24 of the tibial prosthesis 12. This reduces stress and overall wear of the articulating surface.

As seen in FIGS. 4 and 5, the pivot recess 26 comprises a circular opening 28 and undercut circular portion 30. A lip 32 is provided to engage a pivot post 34 on the articulating surface 24. The pivot post 34 has opposed tabs 36, 38 which fit through openings 40, 42 in the lip 32 of the pivot recess. As can be seen in FIGS. 4 and 6, the tabs 36, 38 and the openings 40, 42 are oriented at right angles to each other with respect to the centerline CL. This configuration aids in the assembly of the tibial prosthesis.

At a lateral end 44 of the baseplate 22, an edge 46 is provided. At a medial side of the edge 46 there is an arced groove 48. The arc of the groove 48 comprises a segment of a circle centered on the center of the pivot recess 26. Above the arced groove 48 is an arched lip 50. The arced lip 50 also defines a curve which is a portion of a circle centered on the pivot recess.

At a lateral end 52 of the articulating surface 24, there is an edge 54 which corresponds to the edge 46 on the tibial baseplate. The edge 54 has an arced groove 56 which engages the arced lip 50 of the tibial baseplate and an arced lip 58 which engages the arced groove 48 of the baseplate.

To assemble the prosthetic tibial component 12 of our invention, the pivoting post 34 of the articulating surface is inserted into the pivot recess 26 of the tibial baseplate with the tabs 36, 38 passing through the openings 40, 42. The articulating surface 24 can then be rotated so that the lips 50, 58 on the baseplate and the articulating surface, respectively, engage their respective grooves. When the tibial prosthesis is in use, the action of walking or other movement will cause the articulating surface 24 to rotate slightly around the pivot recess in the baseplate, but the motion will be limited by ligaments and by muscles of the patient so that the lips 50, 58 will not disengage from their respective grooves. At the same time, the area of contact between the articulating surface 24 and the femoral prosthesis 14 will be maximized.

In the preferred embodiment our invention, we have provided a recess 60 in a posterior side 62 of the articulating surface for receiving cruciate ligaments of a patient. A corresponding recess 64 is provided in the baseplate. The articulating surface 24 comprises the medial condylar compartment 28 and a lateral condylar compartment 66 separated by a prominence 68. An anterior side 70 of both the medial and lateral condylar compartments should be raised with respect to a posterior side 72.

The tibial baseplate 12 may be secured to a resected surface on a tibia in any conventional manner including cancellous bone screws, cement, or other means. We prefer to use a central cruciate stem 74 and four generally symmetrically spaced pins 76, 78, 80 and 82. In addition cancellous bone screws may be placed through bores 84, 86 adjacent the cruciate stem. This configuration gives adequate resistance to rotational motion of the tibial baseplate, so that rotational motion can be confined to the interface between the articulating surface and the baseplate.

We claim as our invention:

1. An implantable prosthesis comprising
   a femoral prosthesis adapted to be mounted on a resected distal end of a patient's femur, said femoral prosthesis having
      a medial convex articulating surface for a medial condyle and
      a lateral convex articulating surface for a lateral condyle, and
   a tibial prosthesis adapted to be mounted on a resected proximal end of a patient's tibia, said tibial prosthesis having
      an upper articulating surface comprising
         a medial condylar compartment having an upper surface for slidingly engaging said medial convex articulating surface,
         a lateral condylar compartment for having an upper surface slidingly engaging said lateral convex articulating surface, and
         rotating means extending outwardly from a bottom surface of said medial condylar compartment for rotating said medial and lateral condylar compartments about an axis through said medial condylar compartment
      a base plate comprising
         means for securing said base plate to the resected proximal end of the tibia, and
         means for receiving said rotating means.

2. The implantable prosthesis according to claim 1, wherein the rotating means further comprise a pin and wherein the pivot means comprise a recess.

3. The implantable prosthesis according to claim 2 wherein the pin further comprises at least one tab extending radially outward from said pin and wherein the recess further comprises at least one flange for engaging said tab.

4. The implantable prosthesis according to claim 3 wherein said pin comprises two tabs symmetrically spaced there around and wherein said recess comprises two flanges.

5. The implantable prosthesis according to claim 1 further comprising means for attaching a lateral edge of said upper articulating surface to a lateral edge of said base plate in sliding relationship thereto.

6. The implantable prosthesis according to claim 5 wherein said attaching means comprise a curved flange on said articulating surface and a mating curved groove on said base plate.

7. The implantable prosthesis according to claim 6 wherein said attaching means further comprises a curved flange on said base plate and a mating curved groove on said articulating surface.

8. The implantable prosthesis according to claim 5 wherein said attaching means further comprises a curved flange on said base plate and a mating curved groove on said articulating surface.

9. The implantable prosthesis according to claim 5, wherein the rotating means further comprise a pin and wherein the pivot means comprise a recess.

10. The implantable prosthesis according to claim 9 wherein the pin further comprises at least one tab extending radially outward from said pin and wherein the recess further comprises at least one flange for engaging said tab.

11. The implantable prosthesis according to claim 10 wherein said pin extending radially outward from said pin two tabs symmetrically spaced therearound and wherein said recess comprises two flanges.

12. A tibial prosthesis adapted to be mounted on a resected proximal end of the patient's tibia, said tibial prosthesis comprising:
an upper articulating surface comprising
a medial condylar compartment having an upper surface for slidingly engaging a medial condyle,
a lateral condylar compartment having an upper surface for slidingly engaging a lateral condyle, and
rotating means extending outwardly from a bottom surface of said medial condylar compartment for rotating said medial and lateral condylar compartments about an axis through said medial condylar compartment
a base plate comprising
means for securing said base plate to the resected proximal end of the tibia, and
pivot means for receiving said rotating means.

13. The implantable prosthesis according to claim 12, wherein the rotating means further comprise a pin and wherein the pivot means comprise a recess.

14. The implantable prosthesis according to claim 13 wherein the pin further comprises at least one tab extending radially outward from said pin and wherein the recess further comprises at least one flange for engaging said tab.

15. The implantable prosthesis according to claim 14 wherein said pin comprises two tabs symmetrically spaced therearound and wherein said recess comprises two flanges.

16. The implantable prosthesis according to claim 12 further comprising means for attaching a lateral edge of said upper articulating surface to a lateral edge of said base plate in sliding relationship thereto.

17. The implantable prosthesis according to claim 16 wherein said attaching means comprise a curved flange on said articulating surface and a mating curved groove on said base plate.

18. The implantable prosthesis according to claim 17 wherein said attaching means further comprises a curved flange on said base plate and a mating curved groove on said articulating surface.

19. The implantable prosthesis according to claim 16 wherein said attaching means further comprises a curved flange on said base plate and a mating curved groove on said articulating surface.

20. The implantable prosthesis according to claim 16, wherein the rotating means further comprise a pin and wherein the pivot means comprise a recess.

21. The implantable prosthesis according to claim 20 wherein the pin further comprises at least one tab extending radially outward from said pin and wherein the recess further comprises at least one flange for engaging said tab.

22. The implantable prosthesis according to claim 21 wherein said pin comprises two tabs symmetrically spaced therearound and wherein said recess comprises two flanges.

* * * * *